(12) United States Patent
Vinogradov et al.

(10) Patent No.: US 6,362,175 B1
(45) Date of Patent: Mar. 26, 2002

(54) PORPHYRIN COMPOUNDS FOR IMAGING TISSUE OXYGEN

(75) Inventors: Sergei Vinogradov; David F. Wilson, both of Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 08/137,624

(22) Filed: Oct. 15, 1993

Related U.S. Application Data

(63) Continuation-in-part of application No. 08/022,190, filed on Feb. 25, 1993, now Pat. No. 5,501,225, which is a continuation-in-part of application No. 07/763,184, filed on Sep. 20, 1991, now Pat. No. 5,279,297.

(51) Int. Cl.[7] ............................................. C07D 487/22
(52) U.S. Cl. ...................... 514/185; 514/410; 534/15; 128/654
(58) Field of Search .................. 540/145; 514/185, 514/410; 534/15; 128/654

(56) References Cited

U.S. PATENT DOCUMENTS

| | | | | |
|---|---|---|---|---|
| 4,947,850 A | * | 8/1990 | Vanderkooi et al. | 128/654 |
| 5,238,940 A | * | 8/1993 | Liu et al. | 514/410 |
| 5,280,115 A | * | 1/1994 | Ellis, Jr. et al. | 540/145 |
| 5,284,831 A | * | 2/1994 | Kahl et al. | 540/145 |

FOREIGN PATENT DOCUMENTS

| | | |
|---|---|---|
| EP | 89301924 | 10/1989 |
| EP | 89730076 | 10/1989 |
| WO | WO95/29915 | 11/1995 |

OTHER PUBLICATIONS

Solov'ev et al., Chem. Abst. vol. 100, (1984) 200162*
Morrison and Boyd, Organic Chemistry, Fifth Edition, Allyn and Bacon, Inc. 1987 p. 864.*
Supplemental European Search Report, European Patent Application No. EP 94 93 0778, dated Nov. 18, 1996.

* cited by examiner

*Primary Examiner*—Richard L. Raymond
(74) *Attorney, Agent, or Firm*—Evelyn H. McConathy; Dilworth Paxson LLP

(57) ABSTRACT

Methods and compounds for the measurement in vivo of oxygen in living tissue. The compounds preferably comprise a substituted porphyrin which is soluble in aqueous solution which is capable of absorbing an amount of energy and subsequently releasing the energy as phosphorescent light. In preferred embodiments, the porphyrin has an absorption band which is at a wavelength in the near infra-red window of living tissue and the phosphorescence is quenched by molecular oxygen according to the Stern-Volmer relationship.

46 Claims, 5 Drawing Sheets

US 6,362,175 B1

PORPHYRIN COMPOUNDS FOR IMAGING TISSUE OXYGEN

CROSS-REFERENCE TO RELATED APPLICATIONS

This is a continuation-in-part of U.S. application Ser. No. 08/022,190, filed Feb. 25, 1993, now U.S. Pat. No. 5,501,225, which is a continuation-in-part of U.S. application Ser. No. 07/763,184, filed Sep. 20, 1991, now U.S. Pat. No. 5,279,297.

FIELD OF THE INVENTION

The present invention generally relates to the imaging of the body portions of animals, and specifically to the field of phosphorimetry.

BACKGROUND OF THE INVENTION

This invention is based on the quenching by molecular oxygen of the luminescence of various chemical compounds. This quenching effect can be used for imaging the distribution and concentration of oxygen in body portions of animals, including humans. Such information is indicative of tissue structure and anomalies, defects and diseases associated therewith. For example, certain disease states are characterized by the alteration of oxygen pressure in the involved tissue. The reader is referred to U.S. Pat. No. 4,947,850 for further discussion of the Background of the present invention.

"Luminescence" is the emission of light radiation from a species after that species has absorbed radiation. Luminescence involves the conversion of a molecule to an unstable, excited state. The emission of light arises on the return of the compound to its normal state. "Photoluminescence" refers to luminescence which is associated with excitation by light of substantially short wavelengths. The light emitted from the excited species and which is confined to the period of excitation is fluorescence. The emitted light which persists after excitation has ceased is phosphorescence, or afterglow.

Phosphorescence of certain chemical compounds is quenched by oxygen according to the Stern-Volmer relationship which is stated as follows:

$$T_0/T = 1 + k_Q * T_0 PO_2$$

where $T_0$ and $T$ are the phosphorescence lifetimes in the absence of oxygen, $PO_2$ is the oxygen pressure for a lifetime of $T$, and $k_Q$ is the quenching constant. The constant $k_Q$ is related to the frequency of collisions between the excited triplet state molecule and molecular oxygen and the probability of energy transfer occurring when these molecules collide.

Various and often countervailing considerations are associated with the design, selection and/or preparation of materials for use as phosphorescent probes to study tissue oxygenation. It is generally required that the probe comprises a phosphorescent chromophore, and that the probes be soluble in aqueous solution, for example, physiological media.

The phosphorescent chromophore is the phosphorescent portion of the probe molecule. The chromophore can be converted to the triplet state ($T_1$) by light absorption, followed by return to the ground state either with light emission (phosphorescence and/or delayed fluorescence) or by energy transfer to molecular oxygen.

Phosphorescent oxygen probes which are currently in use are generally based on Group VIII metals, e.g., palladium (Pd) and platinum (Pt) derivatives of porphyrins. See D. F. Wilson et al., *J. Appl. Physiol.*, Vol. 70(6), pp. 2691–92 (1991). The Group VIII metalloporphyrins are advantageous in that they generally have high quantum yields which correspond to the fraction of excited molecules that phosphoresce. The Group VIII metalloporphyrins also possess desirable phosphorescence lifetimes and oxygen-quenching constants. However, these compounds possess serious drawbacks when considered for application to clinical measurements. In this connection, the absorption band of the Group VIII metal porphyrins is generally located at less than about 600 nanometers (nm). Other chromophores which occur naturally in living tissue, for example, hemoglobin, myoglobin and cytochrome, also have absorption bands at wavelengths less than about 600 nm. Due to the overlap in the wavelengths of the absorption bands, the naturally occurring chromophores absorb energy, for example, light, which is used to convert the Group VIII metalloporphyrins from the ground state to the triplet state. This prevents substantial excitation of the probe compounds.

Moreover, penetration of the excitation energy into the tissue is limited to about 50 to about 100 micrometers ($\mu$m) when the excitation light is about 400 nm, and about 500 to about 1,000 $\mu$m when the excitation light is about 560 nm. The penetration limitation is due, at least in part, to the tendency of chromophores which occur naturally in vivo, for example, hemoglobin, to absorb the excitation energy. The absorbance of the naturally-occurring chromophores generally decreases rapidly at wavelengths of greater than about 600 nm which is generally also the absorbance maxima of the currently used phosphorescing probe compounds.

The penetration limitation of excitation energy permits oxygen measurements of only the surface layer of tissue or substantially optically clear tissue, for example, eye tissue. The use of currently available phosphorescing compounds for imaging tissue oxygen is therefore generally limited to clinical pathologies of eye tissue and/or those lying right on or very near the surface of tissue.

Phosphorescent chromophores typically comprise a multiplicity of aromatic ring units. These aromatic ring units generally render the phosphorescent compounds substantially hydrophobic with little or no water solubility. However, it is generally required that phosphorescent compounds for imaging tissue oxygen be hydrophilic and soluble in aqueous solution, for example, physiological media. This aqueous solubility permits the compounds to circulate throughout the circulatory system of the host patient and be delivered to various tissue sites for subsequent excitation and examination and diagnosis of the involved tissue. The hydrophobicity of the currently available phosphorescing compounds generally limits their utility for clinical measurement of tissue oxygenation.

There is thus a need for phosphorescing compounds for studying tissue oxygenation which possess absorbance bands of greater than about 600 nm, this being the absorption maxima of prior art phosphorescing compounds. Moreover, there is a need for phosphorescing compounds for studying clinical pathologies at greater tissue depths and which are substantially soluble in aqueous solution, including physiological media.

SUMMARY OF THE INVENTION

In accordance with the above needs, the present invention provides improved methods and compounds for imaging internal body structures of animals, including humans. The methods and compounds of this invention provide numerous advantages over prior art methods and compounds. In a preferred embodiment, the present invention is directed to a compound for the measurement in vivo of oxygen in living tissue. The compound preferably comprises a chromophore which is capable of absorbing an amount of energy and subsequently releasing the energy as phosphorescent light. The chromophore preferably has an absorption band which is at a wavelength in the near infra-red window of living tissue, and the phosphorescence is quenched by molecular oxygen.

In a more preferred embodiment, the present invention is directed to a compound which is capable of phosphorescing and which has the formula

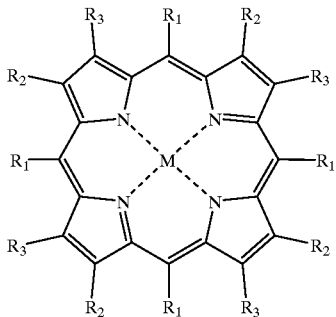

(I)

where $R_1$ is 2(3)-substituted aryl; $R_2$ and $R_3$ are independently hydrogen or are linked together to form substituted or unsubstituted aryl; and M is $H_2$ or a metal.

In additional embodiments, the present invention is directed to a method for measuring the oxygenation of living tissue. The method comprises providing in vivo a phosphorescent compound having an energy absorption band at a wavelength in the near infra-red window of the tissue. The method further comprises causing said compound to phosphoresce and observing quenching by oxygen of the phosphorescence.

Preferred embodiments of methods and compounds taught and claimed herein provide significant clinical tools for examining, diagnosing and treating disease states which result in altered oxygen pressures in affected tissue. Compounds of the present invention are substantially hydrophilic in aqueous solution, for example, physiological media, and possess absorbance bands which are at a wavelength in the near infra-red window of living tissue. In view of their solubility and absorbance characteristics, the present methods and compounds overcome the drawbacks associated with prior art methods and compounds involving phosphorescing materials.

In still additional embodiments, the invention is directed to a method for preparing a compound of the formula

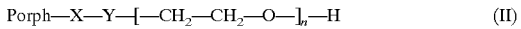
Porph—X—Y—[—CH$_2$—CH$_2$—O—]$_n$—H (II)

wherein Porph is a porphyrin selected from the group consisting of dihydroporphyrin and metalloporphyrin, X is a chemical bond or a linking group selected from the group consisting of —CO— and —NHCH$_2$CO—, Y is a chemical bond or —O—, and n is an integer from about 8 to about 500, comprising:

(a) providing a compound of the formula

Porph—X—Y—Z (III)

where Z is hydrogen, halo or hydroxy; and (b) reacting the compound of formula III with PEG at a temperature and for a time to provide a PEG-substituted porphyrin.

Other features and advantages of the invention are described below in connection with the detailed description of preferred embodiments.

Definitions

As employed above and throughout the disclosure, the following terms, unless otherwise indicated, shall be understood to have the following meanings.

"Aryl", "aryl group" and "aryl system" mean an unsaturated ring system characteristic of benzene. Preferred aryl groups or systems include ring systems of from about 6 to about 14 carbon atoms, and include phenyl, naphthyl, and anthryl, including phenanthryl.

"Alkyl" means a saturated aliphatic hydrocarbon, either branched- or straight-chained. A "lower alkyl" is preferred having about 1 to about 6 carbon atoms. Examples of alkyl include methyl, ethyl, n-propyl, isopropyl, butyl, sec-butyl, t-butyl, amyl and hexyl.

"Alkyloxy" means an alkyl substituted oxy group. Lower alkyloxy groups are preferred.

"Substituted aryl" refers to an aryl group substituted with one or more substituent groups. In preferred embodiments, "substituent group" refers to chemical functional groups which are polar and which render the compounds substituted therewith hydrophilic and substantially soluble in aqueous media. These functional groups are also substantially reactive and are capable of being derivatized and/or of undergoing transformations using standard synthetic organic methodology. Non-limiting examples of preferred substituent groups include halo, carboxy (—CO$_2$R, where R is hydrogen or alkyl), carboxamido, haloformyl (—C(=O)—X, where X is halo), hydroxy (—OH), amino (—NH$_2$) and derivatives thereof, for example, mono- and dialkylamino, glycyl (including —NHCH$_2$CO$_2$H and —C(=O)CH$_2$NH$_2$), sulfonato (—SO$_2$OR, where R is hydrogen or alkyl) and derivatives thereof, for example, halosulfonyl (—SO$_2$X, where X is halo) and sulfonamide (—SO$_2$NH$_2$), and salts or derivatives thereof, including the reaction product of halosulfonyl and glycine. Preferred substituent groups are hydroxy and carboxy and derivatives and salts thereof.

In particularly preferred embodiments, "substituent group" refers to a hydrophilic ligand which is bonded to the chromophore through a covalent or coordinative bond and which renders the compounds hydrophilic and substantially soluble in aqueous media. Preferably, the ligand comprises sugar compounds or hydrophilic residues of flexible, polymeric compounds. The "flexibility" of polymeric compounds refers to the torsional and/or rotational mobility of skeletal bonds in the chain portion of the polymer. In preferred embodiments, the chain portions of the polymeric compounds are highly flexible. Non-limiting examples of preferred flexible polymeric compounds include polymeric residues of proteins, for example, albumin, and polymers of substantially water-soluble monomers, for example, polymers or copolymers of ethylene glycol, propylene glycol, ethylene glycol amine and substituted or unsubstituted sugar compounds, including substituted or unsubstituted mono- and disaccharides. Amino-substituted sugars are preferred substituted sugar compounds, with glucosamine being particularly preferred.

In embodiments where the substituent groups comprise ligands which are covalently linked to the chromophore, the ligands are preferably linked to the chromophores through linking groups. Preferably, the linking groups comprise diradical functional groups, for example, sulfonyl (—SO$_2$—) and carbonyl (—CO—) diradicals.

"Halo" or "halide" means halogen. Preferred halogens include chloride, bromide and fluoride.

"Near infra-red window" refers to the region in the light spectrum where light is only very slightly absorbed by tissue and is located between about 600 nm and about 1300 nm.

"Host patient" refers to animals, including humans, to which the compounds of the invention are administered for measuring tissue oxygen.

"Chromophore" refers to a chemical group which, when present in an aromatic compound, imparts color to the compound by causing a displacement of, or appearance of, absorbent bands in the visible spectrum, and which is capable of being excited from a ground state to an excited state and returning to said ground state by either emitting phosphorescent light or by transferring energy to molecular oxygen.

When a term is used more than once in a chemical formula, each of its meanings is independent of the other.

DETAILED DESCRIPTION OF PREFERRED EMBODIMENTS

Figure 1:
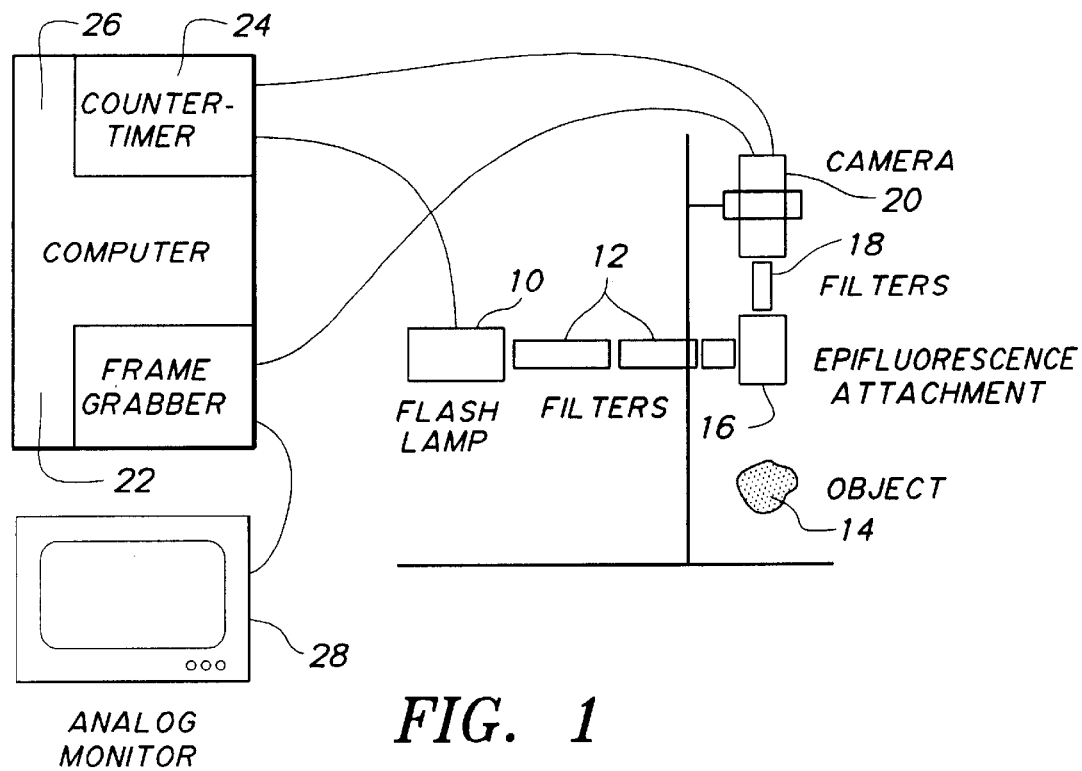
FIG. 1 is a block diagram of one embodiment of an imaging system.

Referring to FIG. 1, a measurement system in accordance with the present invention includes an illuminating light source 10, optical filter(s) 12, a microscope and an associated epifluorescence attachment 16, a long pass cutoff filter 18, a camera 20, a frame grabber 22, a counter timer board 24, a computer 26 and an analog monitor 28. The frame grabber 22 and counter timer board 24 are mounted in the computer 26. In one preferred embodiment the illuminating light source 10 is an EG&G flash lamp with a flash duration of less than 5 $\mu$s; the microscope is a Wild-Leitz Macrozoom microscope; the long pass cutoff filter 18 provides 50% transmission at 630 nm; the camera 20 is a Xybion intensified (gain approximately 18,000) CCD camera with a red sensitive coating on the intensifier and capable of capturing 30 frames per second in its diode storage array;the frame grabber 22 is a Matrox MVP-AT frame grabber; the counter time board 24 is a CTM-05 board (available from MetraByte Corp., Taunton, Mass.); and the computer 26 is an IBM-PC/AT compatible 80386/16 MHZ computer.

According to the present invention, the light from the flash lamp 10 is passed through the optical filters 12, to remove an unwanted portion of the spectrum, and focused on a sample object 14 through the epifluorescence attachment 16; phosphorescence is then observed through the long pass cutoff filter 18. The images are collected with the camera 20 and the frame grabber 22 is used to digitize and average frames while the timing of the flash and gating of the camera intensifier is controlled by the counter timer board 24. The computer 26, operating under the direction of software (not shown) in accordance with the present invention, controls the counter timer board 24, camera intensifier, frame grabber 22 and a computer storage device (not shown). A concise description of a preferred method of operation is provided below with reference to the flowchart of FIG. 2.

The following list briefly enumerates the basic processes or steps of methods for operating the imaging system of FIG. 1 to obtain an oxygen map of a body portion (labelled "object" in FIG. 1) of a subject:

1. Collection of the image of phosphorescence for a given period of time after illumination with the flash lamp.
   a) Preparation of the camera 20 (including clearing of the camera storage array and suppression of the image output).
   b) Firing of the flash lamp 10.
   c) Setting the delay and gating of the camera intensifier (i.e., setting duration of delay and duration the intensifier is on).
   (d) Triggering transfer of the image to the frame grabber 22. This sequence is repeated as many times as the operator requests, typically from 2 to 32 times. The images are averaged in real time.
   (e) Transfer of the averaged image to a computer storage device.
2. Display of the phosphorescence intensity images during the above experimental protocol.

The image is displayed on a monitor for observation by the operator at the end of collection of the average phosphorescence intensity image for each delay time. Each image is displayed until the next image has been collected.

3. Collection of the sequence of images with different delay times after the flash.

The steps of paragraph 1 (or process) above are repeated with the counter-timer board 24 programmed for different delays after the flash according to the sequence requested by the operator. The result is a series of images stored on the computer storage device, each for a different delay time after the flash. A typical sequence of images might consist of delays after the flash of 20 $\mu$s, 40 $\mu$s, 80 $\mu$s, 160 $\mu$s, 300 $\mu$s, 300 $\mu$s and 2,500 $\mu$s, each with a gate width (period of time the intensifier is on) of 2,500 $\mu$s.

4. Analysis of the data:
   a) The images are placed in a computer memory and each is smoothed with a filter to reduce any noise.
   b) The background intensity image is subtracted from all the other images. The background is an image collected with a delay of more than 5 times the phosphorescence lifetime, when the phosphorescence emission is negligible in comparison to the emissions corresponding to the delay periods of interest (e.g., a delay of 2,500 $\mu$s may be used as a background when the lifetimes expected to be measured are from 60 to 600 $\mu$s).
   c) The phosphorescence lifetimes are calculated for each pixel of the image array by a linear regression best fit to a single exponential (i.e., the parameters of an exponentially decaying function or curve are derived). This facilitates the generation of two new two-dimensional maps, one of the initial (zero delay) phosphorescence intensities and one of the phosphorescence lifetimes. The correlation coefficient for the fit of the data to the single exponential is calculated for each lifetime and these are stored as an additional two-dimensional map. Routines for fitting to multiexponential decay may also be included.
   d) The oxygen pressure map is calculated from the phosphorescence lifetime map and the values for $k_q$ and $T_o$ (determined independently in calibration experiments) using the Stern-Volmer relationship:

$$T_o/T = 1 + k_q * T_o * p_{o2}$$

where $T_o$ (also called $\tau o$) represents the lifetime in the absence of oxygen, $k_q$ represents the quenching constant for oxygen and $p_{o2}$ represents the oxygen pressure for a lifetime of T. It is apparent that the above relationship holds whether $p_{o2}$ represents oxygen pressure or oxygen concentration, as each one of those parameters is proportional to the other.

5. Processing of the phosphorescence intensity data:

Data processing software written in C language using the Watcom C Professional version 8.0, 32 bit, 386 protected mode compiler (available from Watcom Systems, Inc., Waterloo, Ontario, Canada). To operate on large amounts of data, the C language program works under an OS/386 Developers kit version 2.1.05 DOS extender operating system (available from ERGO Computing Inc., Peabody, Mass.). The phosphorescence lifetimes and the correlation coefficients are calculated using least squares linear regression. There are additional image processing options designed to optimize the data presentation, including filters for smoothing and edge enhancement, various graphical display options, and pseudocolor. The phosphorescence images and two-dimensional maps are displayed and/or hardcopied by a printer, in accordance with the operator's wishes.

Figure 2:
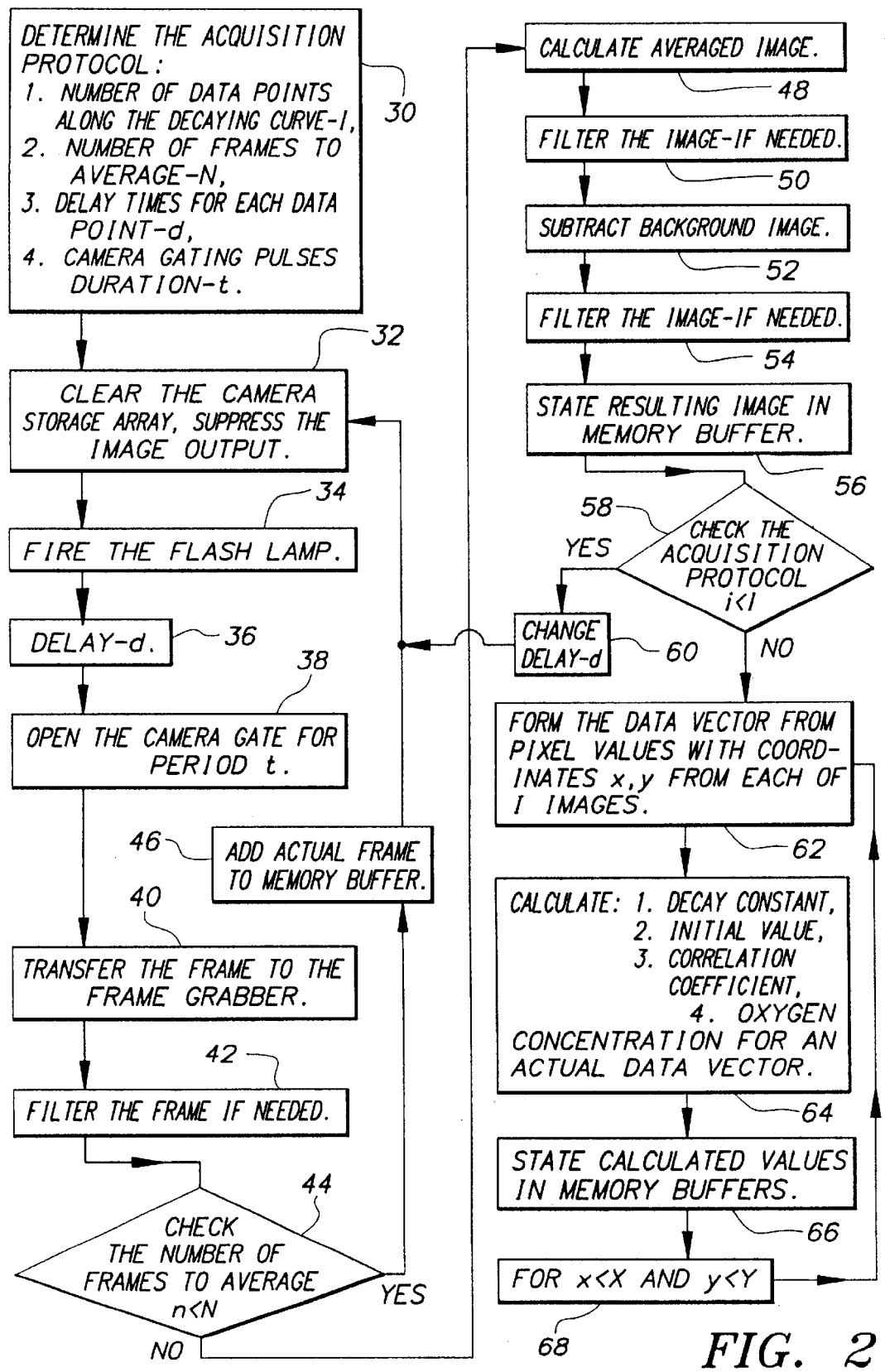
FIG. 2 is a flowchart of one method for oxygen mapping or imaging in accordance with the present invention.

Referring now to the flowchart of FIG. 2, the imaging system of FIG. 1 may be programmed in accordance with the present invention to perform the processes indicated in the respective blocks.

First, as shown in block 30, the computer determines the desired acquisition protocol. That process includes determining the desired number of data points (I) along each decaying luminescence curve (i.e., the number of images to collect), determining the number of frames (N) to average for each image, determining the delay period (d) and determining the duration (t) of each camera gating pulse.

The camera storage array is then cleared and the image output is suppressed (block 32). Next the flashlamp is fired (block 34). The system then waits for the prescribed delay period d (block 36). Next the camera gate is opened for the prescribed period t (block 38). A frame of data is then transferred from the camera to the frame grabber (block 40). Then, if necessary, the captured data frame is filtered (block 42).

At decision block 44 the computer determines whether the number of frames captured (n), which is one after the first pass through the loop, is less than N (the specified number of frames to average). If n is less than N, the program adds the captured frame to a memory buffer associated with the computer and then loops to block 32. If n is equal to or greater than N a composite frame is constructed from an average of corresponding pixels of the N captured frames (block 48). If necessary, the composite frame is filtered to remove noise or otherwise improve the quality of the data (block 50). At block 52 the previously-obtained background data is subtracted from the composite image. The resulting frame after subtraction of the background frame is then filtered as before if necessary (block 54) and stored in memory (block 56). The computer then determines whether the number of data points collected (i) is less than the prescribed number of points (or images) (block 58). The program then changes the delay d (e.g., from 20 μs to 40 μs, from 40 μs to 80 μs, etc.) (block 60) and loops to block 32 if i is less than I; otherwise it proceeds to block 62 and forms data vectors corresponding to the pixels of the I frames of data with indices x, y.

At block 64 the computer calculates decay constants $T_{(x,y)}$ initial values $T_{o(x,y)}$, and oxygen pressure or concentration values $po_{(x,y)}$ for that data vector. The calculated values are then stored in memory (block 66). At block 68 the computer determines whether x and y are less than their respective predefined maximum values (X, Y) and, if so, loops to block 62 to process the remaining pixels. Once the pressure map is obtained a representative image may be displayed using conventional image processing methods. That image may be advantageously employed in the detection of tissue anomalies, defects and diseases.

Figure 3:
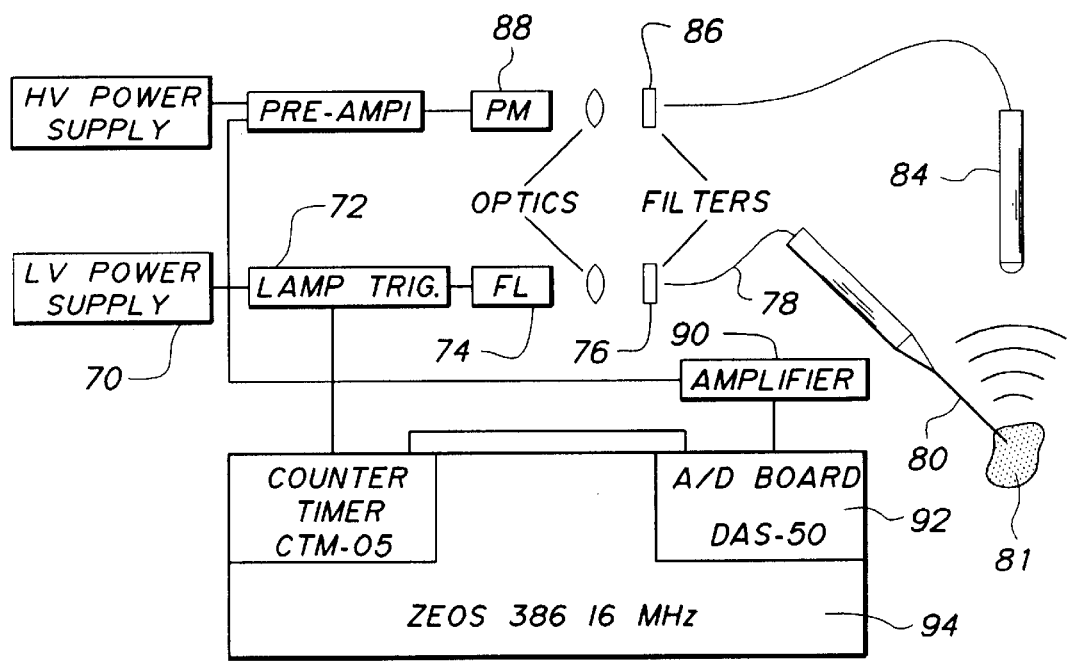
FIG. 3 is a block diagram of a filtering system in accordance with an embodiment of the present invention.
Figure 4:
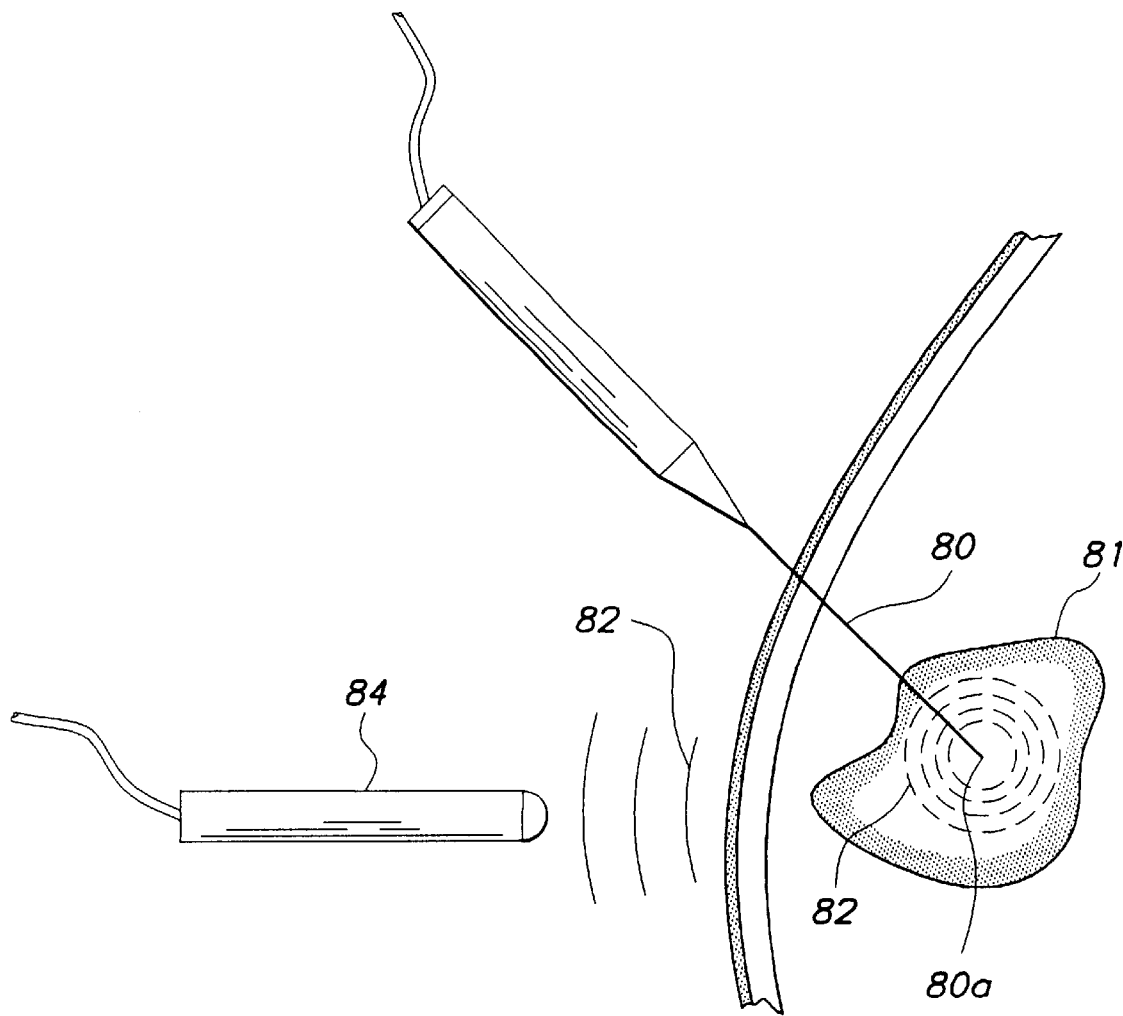
FIG. 4 illustrates a needle light input attachment and light sensor attachment of the present invention.

A more preferred system in accordance with the present invention shown in FIGS. 3 and 4, provides for three dimensional measurements of the oxygen pressure in tissue using a needle phosphorimeter. This embodiment provides for precise measurements of the oxygen pressure in a section of tissue and for the isolation of specific tissue portions. In this preferred system, a phosphorescent probe compound is delivered, for example, by the circulatory system, to the tissue of the patient.

The following discussion is directed to the phosphorescent compounds of the present invention.

The present invention is directed to compounds for the measurement in vivo of oxygen in living tissue. The compounds preferably comprise a chromophore which is capable of absorbing an amount of energy and subsequently releasing the absorbed energy as phosphorescent light. In preferred form, the chromophore has an absorption band which is located at a wavelength in the near infra-red window of living tissue. The phosphorescence is preferably quenched by molecular oxygen.

The compounds of the present invention possess significant potential as clinical tools for examining, diagnosing and treating disease states which result in altered oxygen pressures in the affected tissue. For example, anomalies in the vasculature, such as constrictions, varicosities and aneurisms, generally accompany tumor formation and result in altered oxygen pressures in the diseased tissue. Monitoring of the oxygen pressure thus provides a clinical tool for the diagnosis of diseases.

Various disease states for which the methods and compounds of the present invention are useful for examining and diagnosing are described in U.S. Pat. No. 4,947,850, which is specifically incorporated herein by reference.

The compounds of the present invention preferably comprise a chromophore. Various and well-known compounds are commercially available and/or have been reported in the literature which comprise chromophores including, for example, dyes, examples of which are described in U.S. Pat. No. 4,947,850. Applicants contemplate that these and other chromophore-containing compounds may be used in the method aspects of the present invention, the only requirement being that the chromophore-containing compounds are suitable for administration in vivo.

In this connection, the compounds of the invention are preferably substantially non-toxic towards living tissue and are substantially stable and/or non-reactive in vivo. It is also preferred that the compounds possess a molecular weight and size to promote filtration and excretion of the compounds from the circulatory system of the host patient, as discussed more fully hereinafter.

In preferred form, the chromophore comprises a porphyrin. Porphyrins are physiologically active nitrogenous compounds occurring widely in nature and are derivatives of porphine which has the following formula.

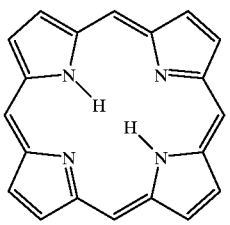

As with porphine, the parent structure of porphyrins typically comprises four pyrrole rings. The hydrogen atoms which are substituted on the pyrrole nitrogen atoms of the porphyrin moiety are replaceable and can be substituted with almost any metal in the periodic table. In certain preferred embodiments, the porphyrin is selected from the group consisting of tetrabenzoporphyrin, tetranapthoporphyrin, tetraanthraporphyrin and derivatives thereof. Other porphyrin compounds which would be suitable for use would be readily apparent in view of the present disclosure.

In accordance with preferred embodiments of the invention, the chromophores are capable of absorbing an amount of energy. Preferably, the chromophore is capable of absorbing an amount of energy which is in the form of light energy, including light having a generally short wavelength.

Applicants have found that suitable chromophores advantageously comprise an energy absorption band which is at a wavelength in the near infra-red window of living tissue. As noted in the above Background of the Invention, the use of phosphorescing compounds for examining and diagnosing living tissue is limited in that the chromophores which occur naturally in living tissue generally absorb the excitation energy, for example, light, which is used to excite the phosphorescent compounds.

The chromophores of the present invention advantageously possess absorption and emission bands which are located in the near infra-red window. Thus, the methods and compounds of the present invention permit examination and diagnosis of clinical pathologies in tissue despite the presence of naturally-occurring chromophores. Moreover, the methods and compounds of the present invention permit the study of pathologies which are located at substantially greater tissue depths as compared to prior art methods and compounds.

The chromophore preferably comprises an absorption band at a wavelength of greater than about 600 nm. In certain preferred embodiments, the chromophore comprises an absorption band in the range from about 600 to about 640 nm. In certain alternate preferred embodiments, the absorption band ranges from about 640 to about 720 nm.

After absorbing an amount of excitation energy, the chromophores preferably release energy in the form of phosphorescent light. The phosphorescence of the compounds of the invention is desirably quenched by molecular oxygen. In preferred embodiments, the phosphorescence is quenched by molecular oxygen according to the Stern-Volmer relationship, which is described hereinbefore. The quenching of the phosphorescence of the compounds of the invention is desirably unaffected by, and is independent of, the pH of the surrounding medium.

As with the absorption characteristics described above, the chromophore preferably comprises an emission band at a wavelength which is located also in the near infra-red window of living tissue. Preferably, the emission band is located at a wavelength of greater than about 600 nm, with a wavelength of greater than about 600 nm to about 1300 nm being preferred.

An important and critical requirement of the compounds of the present invention is that they are substantially soluble in aqueous media, for example, physiological media. Aqueous solubility is generally necessary for the compounds to circulate throughout the body of the host patient via the circulatory system and to be delivered to the affected tissue, for example, diseased soft body tissue. As noted above, chromophores are generally aromatic in nature and therefore hydrophobic. However, applicants have found that chromophores are desirably and advantageously substituted with at least one substituent group, as defined above and as described more fully hereinafter, which imparts substantial aqueous solubility to the chromophores.

In accordance with preferred embodiments of the present invention, the phosphorescing compounds have the following formula:

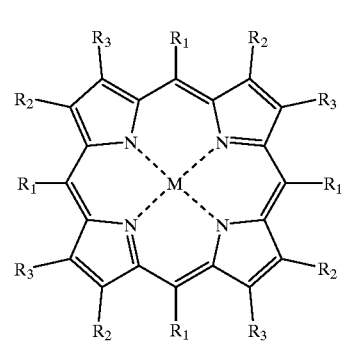

(I)

where $R_1$ is substituted or unsubstituted aryl; $R_2$ and $R_3$ are independently hydrogen or are linked together to form substituted or unsubstituted aryl; and M is $H_2$ or a metal.

As is apparent to those skilled in the art, when $R_2$ and $R_3$ are linked together to form an aryl system, the aryl system is necessarily in a fused relationship to the respective pyrrole substrate.

Preferably, M is a metal selected from the group consisting of Zn, Al, Sn, Y, La, Lu, Pd, Pt and derivatives thereof. Non-limiting examples of suitable metal derivatives include LuOH, YOH, AlOH and LaOH.

In certain preferred embodiments, the compounds of the present invention are tetrabenzoporphyrin (hereinafter "TBP") compounds, which correspond to the compound of formula I above wherein vicinal $R_2$ and $R_3$ groups are linked together to form benzene rings which are fused to the respective pyrrole rings. Also preferred are tetranaphthoporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings.

Unless indicated otherwise, or unless apparent from the disclosure, further reference herein to "TBP" compounds is understood to refer also to TNP and TAP compounds.

Preferred TBP compounds have the following formula

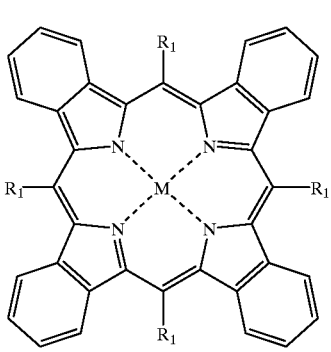

(IV)

wherein R, and M are as defined above. Particularly preferred TBP compounds are metallotetrabenzoporphyrin (hereinafter "MTBP") compounds where M is a metal or metal derivative as described hereinbefore.

TBP compounds of formula IV above were synthesized by template condensation of potassium phthalimide with sodium acetate (or sodium phenylacetate) in the presence of zinc acetate (See, for example, V. N. Kopranenkov et al., *J. Gen. Chem.* (Russ), Vol. 51(11), pp. 2165–68 (1981) and V.

N. Kopranenkov et al., *J. Org. Chem.* of USSR, Vol. 15(3), pp. 570–75 (1979)) as described in the following equation:

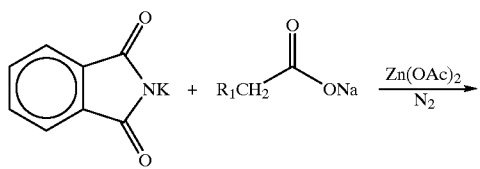

(1)

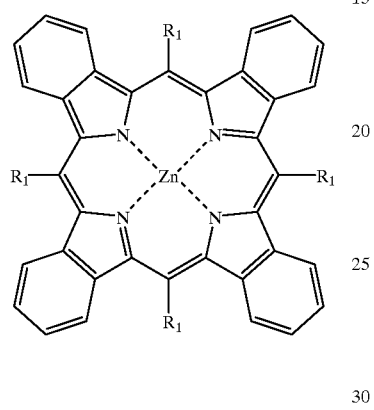

where $R^1$ is defined as above. The reaction mixture is preferably heated to a substantially elevated temperature, for example, about 360° C, for about 40 minutes.

Zinc acetate in the above reaction can be replaced with zinc benzoate. However, this substitution fails to increase the yield of the reaction significantly. See K. Ichimura et al., *Inorg. Chim. Acta.*, Vol. 182, pp. 83–86 (1991).

The product from the reaction of equation 1, zinc tetrabenzoporphyrin (hereinafter "ZnTBP"), was reduced to the dihydro product by heating in a mixture of acetic and phosphoric acids as described in the following equation:

(2)

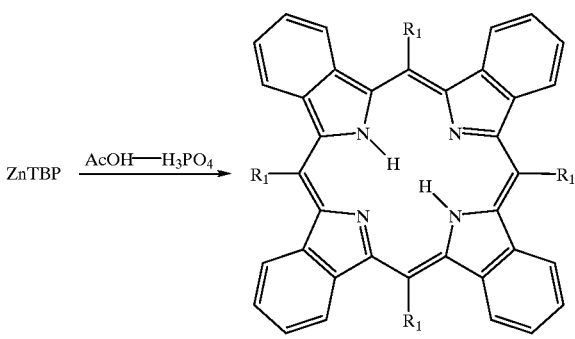

wherein $R_1$ is defined as above. Preferably, the acetic and phosphoric acids are mixed in a ratio of about 1:3 and the reaction mixture is heated to about 80° C. The reaction is substantially complete in about 2 hours.

The dihydrotetrabenzoporphyrin product from the above reaction (hereinafter "$H_2TBP$"), was purified by flash chromatography on an alumina ($Al_2O_3$) column. Metal insertion was carried out in an imidazole melt as set forth in the following equation:

(3)

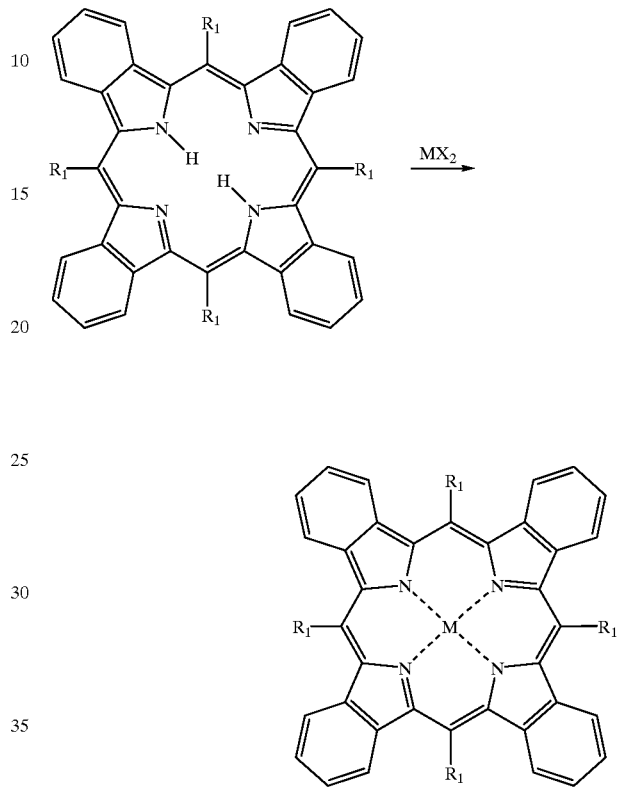

wherein $MX_2$ is a source of metal ions and preferably corresponds to chlorides, bromides and acetates of metals. Metal acetates are preferred sources of metal ions as compared to the corresponding halides. Palladium acetate (Pd $(OAc)_2$) is particularly preferred and provided 99% conversion to the metal complex in refluxing tetrahydrofuran (THF).

The reaction of equation 3 is preferably conducted at elevated temperatures, for example, temperatures greater than 100° C. Preferably, the reaction is conducted at a temperature of about 200° C., and the reaction is substantially complete after about 1 hour.

Particularly preferred among the TBP compounds are the compounds of formula IV above where at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TPhTBP") compounds, including meso-tetraphenyltetrabenzoporphyrin (hereinafter "m-TPhTBP") compounds, which have the following formula:

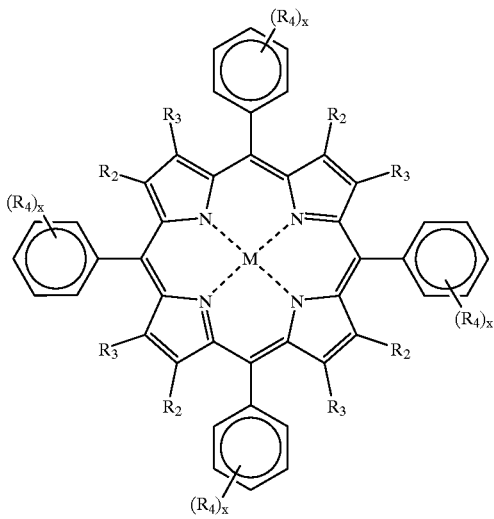

(V)

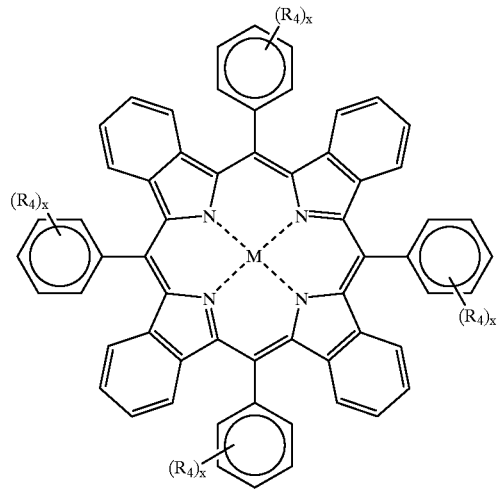

-continued where R$_2$, R$_3$ and M are as defined above, R$_4$ is a substituent group, and x is an integer from 0 to 3. Particularly preferred TPhTBP compounds are substituted compounds of formula V where x is an integer from 1 to 3.

In connection with the preferred substituted compounds of the invention, Applicants have found that substituent groups impart desirable properties to the compounds. For example, compounds which comprise substituent groups are characterized by solubility in polar solvents, including aprotic solvents, such as dimethylformamide (DMF), acetone and chloroform (CHCl$_3$), and protic solvents, such as water. The degree of substitution and the nature of the substituent groups may be tailored to obtain the desired degree of solubility and in the desired solvent or solvent mixture.

Similarly, applicants have found that the present compounds are preferably substituted with substituent groups to regulate their rate of excretion from, and/or metabolism in, biological systems. For example, the substituent groups cause the compounds to desirably remain in the body of the host to which they are administered for a period of time to permit imaging of the oxygen in the body tissue, but not for extended and unnecessary periods of time.

The substituent groups are preferably substituted on the chromophore portion of the compounds of the invention. The term "chromophore portion" includes, for example, the atoms in the compound of formula I which are immediate to the porphyrin moiety, as well as the R$_1$, R$_2$ and R$_3$ groups. Preferably, the substituent groups do not negatively affect or alter the absorbance and/or emission characteristics of the chromophores.

Applicants have found that particularly desirable rates of excretion and/or metabolism of compounds in biological systems is obtained with substituted TPhTBP compounds of formula V above. Such substituted TPhTBP compounds may be synthesized by condensing substituted benzaldehyde with pyrrole in a solvent as set forth in the following equation.

(4)

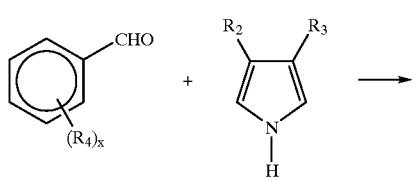

wherein R$_2$, R$_3$, R$_4$, M and x are as defined above.

In the above reaction, the compounds of formula V may be obtained directly as the metalloporphyrin. In this case, the reaction is conducted in the presence of a metal ion source. Metal acetates, for example, zinc acetate (Zn(OAc)$_2$), are preferred sources of metal ion. Preferred solvents are polar, aprotic solvents, for example, dimethylformamide (DMF). In addition, the reaction of substituted benzaldehyde with pyrrole is preferably conducted at a temperature and for a time to obtain the porphyrin compounds of formula V. In preferred embodiments, the reaction is conducted at a temperature of from about room temperature to about 200° C., with a temperature of from about 50° C. to about 180° C. being preferred, and a temperature of about 153° C. being more preferred.

In addition, the reaction is preferably conducted for a period of from about 5 minutes to about 24 hours, with a period of from about 1 hour to about 16 hours being preferred, and a period of about 10 hours being more preferred.

Substituent groups in PhTBP compounds may be bonded to the phenyl ring(s) at the 2-, 3- or 4-position. In certain instances, the substituents are preferably and advantageously bonded to the phenyl ring(s) at the 2- and/or 3-positions. These compounds are referred to hereinafter as "2(3)-substituted PhTBP" compounds. The 2(3)-substituted PhTBP compounds possess desirable properties as compared to PhTBP compounds having other substitution patterns, for example, PhTBP compounds where the phenyl group(s) are substituted at the 4-position(s). In particular, and as discussed more fully hereinafter, it is contemplated that certain 2(3)-substituted PhTBP compounds possess hydrophilicities and geometries which permit their ready excretion from the body of the host patient and therefore do not remain in the circulatory system of said host for unnecessary and undesirably extended periods of time.

As noted above, the substituent group comprises hydrophilic ligands, for example, sugars and residues of flexible, hydrophilic polymeric compounds, in certain particularly preferred embodiments. The hydrophilic ligands are preferably linked to the chromophore to impart substantial hydrophillicity and stability to the chromophore, particularly in aqueous solutions, including physiological media. The chromophore and the ligand preferably remain linked or bound together after administration of the compounds to the host patient and during imaging of the tissue oxygen.

Applicants have found that by remaining bound or linked together, the ligand advantageously protects the chromophore from chemical transformations in vivo during the imaging procedure. Without intending to be bound by any theory or theories, it is contemplated that protection of the chromophore results from the formation by flexible polymeric ligands of globular structures around the chromophore. The chromophore moieties are thereby "encased" in the globular structures and are protected from chemical transformations, degradation, and the environment surrounding the compounds, generally.

In preferred embodiments, the ligand is coordinatively linked to the chromophore. Coordinative bonds may occur, for example, where the ligand comprises the residue of compounds which comprise hydrophobic moieties, for example, sugar and protein compounds. Applicants contemplate that the coordinative bonds arise from hydrophobic-hydrophobic interactions between the chromophores and hydrophobic moieties of the ligands.

In alternate preferred embodiments, the ligand is covalently linked to the chromophore. In this embodiment, a covalent bond is formed between at least one atom of the ligand and at least one atom of the chromophore. Such covalent bonds may be formed using standard organic synthesis techniques.

The following discussion is directed to the observation that compounds of the invention which comprise substituent groups have improved solubility in aqueous media, including biological fluid, and improved rates of excretion from the body of the host patient. As known to those skilled in the art, nephrons of the kidneys regulate the composition of blood by a combination of processes, including filtration. Porous capillaries and podocytes in the nephrons function as filters. Water and small solute molecules generally pass through the filter, while blood and larger molecules, for example, plasma proteins, are retained in the capillaries.

The porous capillaries and podocytes comprise porous filters which comprise openings that are sized to allow substantially spherical molecules having molecular weights of up to about 20,000 Daltons to pass through for excretion from the body. However, filtration of the molecules is substantially a function of the diameter of the individual solute molecule. Thus, molecules which have molecular weights of less than about 20,000 Daltons, but which have substantially large diameters, are unable to pass through the porous filters.

While not intending to be bound by any theory or theories, applicants contemplate that the geometry of PhTBP compounds, and particularly, TPhTBP compounds, is such that substituents at the 2(3)-position of the phenyl rings are generally located within the circumference of the TPhTBP compounds, as defined by the carbons at the 4-positions of the phenyl rings. This imparts a substantially smaller diameter to the 2(3)-substituted TPhTBP compounds in comparison to, for example, the corresponding 4-substituted TPH-TBP compounds. Applicants contemplate that substituents at the 4-position generally lie outside of the circumference of the TPhTBP compounds. Accordingly, TPhTBP compounds which comprise hydrophilic ligands, and particularly ligands comprising substantially high molecular weight polymeric compounds which are substituted at the 4-position(s) of the phenyl rings, are generally unable to pass through the pores of the capillaries and podocytes.

In contrast, the 2(3)-substituted TPhTBP compounds are generally capable of passing through the pores of the capillaries and podocytes and are readily excreted from the body of the host patient. The 2(3)-substituted TPhTBP compounds do not remain in the circulatory system of the host patient for undesirably extended periods of time.

Applicants have found that the chromophore compounds which are substituted with one or more polar radicals and which have substantial water solubility are capable of binding to hydrophilic ligands either in vitro or in vivo. Applicants contemplate that the chromophores may be bound to ligands according to the methods taught herein and prior to administration to the host patient. The "pre-liganded" chromophore is than administered to the host patient, for example, by injecting the host patient with an aqueous solution thereof.

Alternatively, polar chromophores which are not bound to ligands may be administered to a host patient for binding with ligands in vivo. The polar chromophores, and particularly carboxy, oxy and amino-group substituted metalloporphyrins, including metalloporphyrins which are substituted with a chemical group that is the reaction product of sulfonato and glycine, bind in vivo with albumin which is naturally present in the body, and form stable water soluble complexes which have strong oxygen dependent phosphorescence. Similarly, the chromophores and the ligand, for example, polymers of ethylene glycol, may be administered separately to the host patient, and binding in vivo may occur between the chromophore and the administered ligand.

The following discussion is directed to methods for covalently linking together ligands and chromophores. Applicants have found that tetraphenylated compounds can be converted to chlorosulfonato derivatives as set forth schematically in the following equation.

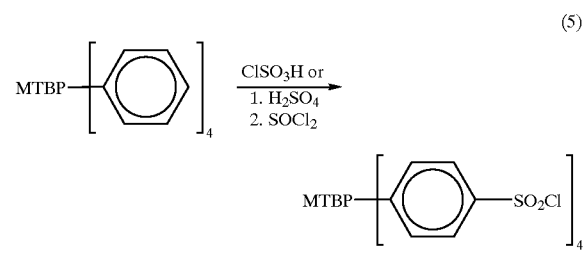

(5)

Amines, for example, primary and secondary amines, such as glycine, 4-aminophenylacetic acid, glucosamine and high molecular weight amines, including polyethylene glycol amine and amino group-containing polysugars, can be reacted with the chlorosulfonato derivatives to give the corresponding covalently linked tetraphenylated sulfonamides. A similar procedure was reported in the literature for derivatization of copper phthalocyanine benzo-rings in the preparation of water-soluble dyes. See H. Mozer, *Phthalocyanines*, ACS Monogr. Ser., Chapter 5 (1969).

Alternatively, the chlorosulfonato derivatives may be hydrolyzed to the corresponding sulfonic acid derivatives. Although the sulfonic acid derivatives are substantially water-soluble, applicants have found that they tend to form non-phosphorescent aggregates in aqueous media and, therefore, are not particularly suitable for use as oxygen probes.

Palladium and platinum tetraphenylated porphyrin compounds are stable towards treatment with chlorosulfonic acid and may be used for further derivatizations. However, applicants have found that metal ions, for example, Al, Lu, La and Y, may be displaced from certain metalloporphyrin compounds during treatment with chlorosulfonic acid. Applicants have found that these latter porphyrin compounds may be derivatized by preparing initially the sulfonato derivative of the hydrogenated porphyrin compound; inserting a suitable metal ion; and converting the sulfonate to the corresponding chlorosulfonate. The chlorosulfonate is then reacted with suitable reactants, for example, amines, as described above.

In alternative embodiments, carboxy-substituted chromophore compounds may be esterified with polyethylene glycol and/or polypropylene glycol compounds. For convenience, polyethylene glycol and polypropylene glycol compounds are collectively referred to hereinafter as "PEG compounds". PEG compounds of varying molecular weights are well known to those skilled in the art, and are generally non-toxic, chemically stable and inert alcohols. PEG compounds are also generally polar and hydrophilic, and impart desirable aqueous solubility properties to the chromophore compounds. Accordingly, PEG compounds are particularly suitable for use as alcohols and for esterification of polar substituted chromophore compounds.

Applicants have developed general methods for esterifying carboxyl containing porphyrins with PEG compounds to provide compounds of the following general formula:

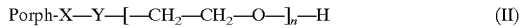

Porph-X—Y—[—CH$_2$—CH$_2$—O—]$_n$—H  (II)

wherein Porph is a porphyrin selected from the group consisting of dihydroporphyrin and metalloporphyrin, X is a chemical bond or a linking group selected from the group consisting of —CO— and —NHCH$_2$CO—, Y is a chemical bond or —O—, and n is an integer from about 8 to about 500. In preferred embodiments, X is —CO—and Y is —O—. Also in preferred embodiments, n is an integer from about 10 to about 100 and more preferably, about 20.

The methods for preparing PEG-substituted porphyrin compounds are based on the reaction of PEG with porphyrin carboxylic acids and acid halides, which may be formed in situ, and which are represented by the formula

Porph-X—Y—Z  (III)

wherein X and Y are as defined above, and Z is hydrogen, hydroxy or halo. It is understood that when X and Y are both chemical bonds in the compounds of formula III, the substituent Z is bonded directly to the porphyrin moiety and is preferably hydroxy or halo. Preferably, the methods are based on the reaction of PEG with porphyrin acid halides.

In preferred embodiments, the formation of the porphyrin acid halide involves reacting an appropriately substituted porphyrin compound, for example, the compound of formula V where R$_4$ is —CO$_2$H and x is an integer from 1 to 3, with an inorganic halogenating agent, for example, thionyl chloride (SOCl$_2$), or an organic halogenating agent, for example, oxalyl chloride. Preferably, the substituted porphyrin is carboxy-substituted porphyrin and the acid halide is thionyl chloride.

The carboxy-substituted porphyrin is reacted with the halogenating agent under suitable reaction conditions to promote formation of the acid halide. For example, the reaction may be conducted in a solvent, such as tetrahydrofuran (THF), for several hours at room temperature.

Applicants have found that the reaction of PEG with the substituted porphyrin may be advantageously carried out in an excess of PEG and without any additional solvents. Under these reaction conditions, PEG behaves as both a reactant and a solvent.

The reaction of the compound of formula III with PEG is preferably conducted with PEG having an average molecular weight (Avg. MW) of about 350 to about 10,000, with an Avg. MW of about 1,000 to about 4,000 being preferred. More preferably, the PEG has an Avg. MW of about 1,500.

The reaction is preferably conducted at a temperature and for a time to promote substantially complete esterification and formation of the PEG-substituted porphyrin. Suitable reaction temperatures range from about room temperature to about the reflux temperature of PEG. Preferably, the reaction is conducted at a temperature of about 100° C. to about 150° C. Suitable reaction times are from about several hours to several days, with a reaction time of about 24 hours being preferred.

The preparation of the compound of formula II involves also separation and purification of the final product from the excess of PEG. Suitable separation and purification techniques include membrane ultrafiltration and size exclusion chromatography. The degree of purification of the final product may be monitored by absorption measurements.

Preparation of specific compounds of the present invention is described more fully hereinafter in connection with the working examples.

Applicants contemplate that thin films of porphyrin compounds which are liganded to PEG compounds may be prepared and readily introduced into the structures of polymers, for example, plastic materials. Thus, the PEG-derivatized compounds may be used as oxygen sensitive ingredients in a wide range of synthetic materials.

In accordance with the present invention, a light flash system having a frequency of less than 5 μs half time is used for excitation of the phosphorescent material. In a preferred embodiment, the flash system includes a low voltage power supply 70 which powers a lamp trigger 72 and flash lamp 74. Light from the flash lamp 74 is filtered 76 and reduced so as to propagate along a 0.2 mm fiber light guide 78. The distal end of the light guide 78 is encased within a needle 80. The light guide extends axially through the needle 80. The needle 80 can be inserted into body tissue or a body portion 81 in a manner analogous to that of microdialysis probes.

The excitation light emitted from the distal end 80a of the needle 80 is scattered by the tissue and absorbed. Upon exciting the phosphorescent probe, the excitation light causes the emission of phosphorescent light having a radius of visibility 82. Referring to FIG. 3, the radius 82 of the illuminated volume of tissue (the sample tissue volume) may be adjusted by altering the wavelengths of the excitation light. The radius will be between about 50 to 100 μm when the excitation light has a wavelength of 415 nm, and between about 0.5 to 1 mm when the excitation light has a wavelength of 530 nm.

The emitted light signal, which has a wavelength greater than about 650 nm is not significantly absorbed by the tissue and is randomly scattered through the tissue. The phosphorescence emission is then collected by a collector lens system 84 placed near the tissue surface. The collected emission is filtered 86 and the signal conducted to a photomultiplier 88 for detection. The resulting signal is amplified 90 and the phosphorescence decay curve determined. In a preferred embodiment, the signal is digitized with, for example, a 12 bit, 1 MHz A/D board 92, and then analyzed with a microcomputer 94.

Because the phosphorescence is emitted only from the volume of tissue which is exposed to the excitation light at the end of the needle 80, the phosphorescence lifetime is an accurate measure of the oxygen pressure in the blood for that volume of tissue.

The system of this embodiment may utilize data handling and analysis including deconvolution routines for determining the fit of the decay to a single or multiple exponentials. In a uniform environment, the decay of the oxygen is a single exponential, thereby allowing quantitative calculation of the oxygen pressure in the immediate environment of the needle tip. With the method and apparatus of the embodiment of FIGS. 3 and 4, it is possible to make rapid repetitive measurements of phosphorescence lifetime (to at least 20 times per second), thereby providing excellent temporal and spatial resolution of the changes in oxygen pressure.

The distribution of the oxygen in the tissue may be determined by attaching the needle 80 to a holder device which allows precise orientation and controlled depth of insertion into the tissue. As the needle 80 is inserted, the phosphorimeter is used to continuously measure the phosphorescence lifetime. A graph can then be made of the oxygen pressure verses depth or spatial orientation in the tissue.

The insertion of the needle at multiple places in the tissue provides for the generation of a three dimensional map of the oxygen pressure. It is to be appreciated that variations in the intensity of the measured phosphorescence with respect to position or depth in the tissue, does not affect the oxygen measurement, as the phosphorescence lifetime is independent of this parameter, as discussed in U.S. Pat. No. 4,947,850.

The embodiment of FIGS. 3 and 4 thus utilizes three properties of the phosphorescence method which make it superior to existing technology, such as the use of microoxygen electrodes. Initially, the excitation light for some of phosphorescent probes is preferably within the wavelength range of 400 to 600 nm. Within this wavelength range, the tissue absorption varies from very strong in the blue region (400 to 450 nm) and gradually progresses to weak absorption in the red region. Throughout this wavelength range, the tissue absorbance determines the distance from the needle that will be illuminated by the flash of the excitation light. The measured phosphorescence must originate from the illuminated section of tissue sampled to be varied from about 100 um to greater than 1 m, subject to the choice of the operator. Oxygen electrodes, in contrast, sample only oxygen diffusing to the electrode tip, maximizing the effects of tissue damage on the measurements.

Second, the emitted phosphorescence is in the near infrared region of the spectrum, having a wavelength of from about 630 to 950 nanometers. Tissue absorption is very weak at this wavelength. Thus, the phosphorescence emitted from the illuminated region near the tip of the needle is scattered but not absorbed. The emitted phosphorescence can travel long distances through the tissue to the surface where it leaves the tissue and can be collected by the collector. Only the excitation light need be transmitted through the needle, and the phosphorescence can be collected with high efficiency using a large collector lens.

The invention will now be illustrated in more detail with reference to the following specific, non-limiting examples.

General Considerations

Solvents for phosphorescence measurements were degassed by three freeze-pump-thaw cycles and stored in a vacuum over sodium benzophenone ketyl (THF) or 4 Å molecular sieves (DMF). The solvents were vacuum transferred immediately prior to the phosphorescence measurements and samples were sealed under high vacuum.

An enzymatic system (glucose-glucose oxidase-catalase) was used for deoxygenation of aqueous solutions and $N_2$-$O_2$ gas mixtures containing either 2.89% of oxygen or 20% oxygen (air) were used for calibration and measurements of the quenching constants.

Solvents for chromatography and synthesis: chloroform (Aldrich), methylene chloride (Aldrich), ether (Aldrich), petroleum ether (Aldrich), pyridine (Fisher), THF (Fisher), DMF (Fisher) were used as purchased.

All reagents were used as purchased from Aldrich Chemical Co. or Sigma Chemical Co.

Absorption spectra were recorded on a Beckman DU-64 spectrophotometer. Emission spectra (fluorescence and phosphorescence) were recorded using an AMINCO SPF-500C spectrofluorimeter. $^1H$ NMR spectra were recorded using a Brucker 300 MHz instrument. Phosphorescence lifetime measurements were performed using a light guide phosphorimeter designed by applicants. HPLC analysis of reaction mixtures was carried out on a SpectraPhysics 8800 gradient system, using an Adsorbosphere HS C4 100×4.6 mm column and methanol:water mixture as a mobile phase.

EXAMPLE 1

This example is directed to the synthesis of palladium (Pd) tetraphenyltetrabenzoporphyrin.

Potassium phthalimide (3.89 g, 21 mmol), sodium phenyl acetate (6.61 g, 41.79 mmol) and zinc acetate dihydrate (2.04 g, 9.31 mmol) were combined and placed in a glass U-tube. The mixture was heated to 360° C. in a constant flow of dry nitrogen. After 40 min., the tube was cooled and the resulting dark brown solid was collected. The filtrate was repeatedly washed with hot water and then dried. The resulting powder was placed in a round-bottomed reaction flask and glacial acetic acid (10 ml) and concentrated phosphoric acid (30 ml) were added to the flask. The mixture was heated with stirring for 2 h and then diluted with water (300 ml). The precipitated solid was filtered and washed extensively until the water extract had a pH of about neutral. The reaction product was dried in vacuum, dissolved in pyridine (15 ml) and chromatographed (column: 50 cm height, 4 cm diameter; packed with $Al_2O_3$ (Brockman, Neutral)) in petroleum ether. The reaction products were chromatographed first with a mixture of petroleum ether-:chloroform (10:1) and a small fraction of yellowish-brown compound was collected. Subsequent flash chromatography with pyridine:chloroform (1:10) gave a deep green solution which was spectroscopically identified as the tetraphenylated derivative of $H_2TBP$, referred to hereinafter as "$H_2TPhTBP$". The green solution was concentrated by rotary evaporation and vacuum dried to yield 1.8 g (11%) of $H_2PhTBP$.

Insertion of Pd: Imidazole (2 g), $H_2TPhTBP$ (100 mg, 0.2 mmol) and $Pd(OAc)_2$ (40 mg, 0.25 mmol) were placed in a small reaction vial, melted and stirred at 170–200° C. After 15–20 min, spectral analysis of the sample showed total conversion to the metal chelate and the reaction was stopped. The resulting solid was diluted with water and the precipitate was collected by centrifugation and dried under vacuum. Flash chromatography on an $Al_2O_3$ column (pyridine:chloroform 1:10) followed by prolonged vacuum drying gave PdTPhTBP (103 mg, 0.11 mmol) (Yield 85%).

EXAMPLE 2

This example is directed to the synthesis of lutetium (Lu) tetraphenyltetranaphthoporphyrin.

2,3-Naphthalenedicarboximide (2 g, 10.1 mmol), phenyl acetic acid (1.6 g, 12 mmol), zinc acetate dihydrate (1.55 g, 7.08 mmol) and potassium bicarbonate (1.01 g, 10.1 mmol) were combined in a glass U-tube and subjected to reaction conditions as described in Example 1 with respect to TBP. Flash chromatography of the crude acid treated product gave a dark brownish-green solution which was spectrascopically identified as dihydrotetraphenyltetranaphthoporphyrin ("$H_2TPhTNP$"). The filtrate was concentrated to provide 0.35 g of dry product with a yield of 14%.

Insertion of Lu: $LuCl_3.6H_2O$ (40 mg, 0.1 mmol) was added to $H_2TPhTNP$ (50 mg, 0.05 mmol) in melted imidazole (2 g) and heated (150–1700) with stirring for 30 min. The resulting mixture was dissolved in $CH_2Cl_2$ and washed several times with water in a separatory funnel. The resulting solution was dried and chromatographed on an $Al_2Cl_3$ column. The $CH_2Cl_2$ solution was concentrated to provide the desired product (LuTPhTNP) with a yield of 35 mg (79%). An amount of Lu(OH)TPhTNP was obtained also. Applicants contemplate that the initial product comprised one or more chlorine atoms bound to the lutetium atom of the metalloporphyrin which was hydrolyzed to give the corresponding hydroxy compound. It is well known that lanthanides have a very high oxophilicity.

Applicants contemplate that the corresponding 1,2-naphthoporphyrin compounds may be prepared using similar synthetic techniques.

EXAMPLE 3

This example is directed to the synthesis of meso-tetra-(orthophenyl-substituted) porphyrin compounds.

Approximately 25 ml of N,N-dimethylformamide (DMF) is heated to reflux in a 100 ml round-bottomed flask. Pyrrole and 20 mmol of either 2-carboxybenzaldehyde or 2-hydroxybenzaldehyde (salicylaldehyde) is added. After 10 minutes at reflux, 5 mmol of zinc acetate is added and the reflux is continued overnight. The next morning the reaction is terminated and the porphyrin is precipitated from solution by pouring the reaction mixture into water (100 ml). The crude product is collected by filtration and the zinc porphyrins are purified by standard chromatographic techniques. The zinc is removed by heating the product in a 1:3 mixture of glacial acetic acid and phosphoric acid for 4 hours. Pd or other metal ions are inserted by mixing the free porphyrin with imidazole and heating to 220–250° C. The metal salt is then added to the imidazole melt and heating continued until the metal-porphyrin complex is fully (>98%) formed.

EXAMPLE 4

This example is directed to the synthesis of the sulfonamide adduct of PdTPhTBP and 4-aminophenylacetic acid.

PdTPhTBP (100 mg, 0.1 mmol) and chlorosulfonic acid (3 ml) were combined in a 5 ml reaction vial. The mixture was stirred for 2 h and then added dropwise to ice cold water (50 ml) saturated with NaCl. The resulting suspension was centrifuged and washed with cold water several times. The product was dried on a vacuum line and dissolved in DMF (5 ml). A five-fold molar excess of 4-aminophenylacetic acid and one drop of pyridine were added and the mixture was stirred at room temperature for 24 h. The resulting deep green solution was poured into water and the pH adjusted to 3 by addition of HCl. Precipitated solid was collected by centrifugation and washed with water until the pH of the wash solution was neutral. Vacuum drying of the precipitated solid provided the desired product with a yield of 119 mg (67%). The resulting sulfonamide was soluble at alkaline pH and absorption spectra indicated broadening of both Soret and Q bands.

EXAMPLE 5

This example is directed to the synthesis of PEG-modified Pd meso-tetra-(4-carboxyphenyl)porphyrin.

Palladium meso-tetra-(4-carboxyphenyl)porphyrin ("PdTCPP") (80 mg, 0.09 mmol) and THF (8 ml) were placed in a 10 ml reaction flask equipped with an air-cooled condenser. A four- to five-fold molar excess of $SOCl_2$ (0.2 ml) was added to the reaction flask by syringe and the mixture was stirred. After the PdTCPP powder was dissolved (~2 h), the reaction mixture was stirred for one additional hour and then 3 ml of methoxypolyethyleneglycol (avg. molecular weight of 350) was added to the reaction mixture. The mixture was stirred for one hour at room temperature and then heated to reflux. After refluxing for approximately 3 h, the THF was completely evaporated and further reaction was carried out in PEG as solvent. Progress of the reaction was monitored by using HPLC analysis of the hydrolyzed samples. Sequential formation of one-, two-, three- and four-substituted porphyrins was clearly evident from the chromatograms. Reaction was stopped when >98% of starting PdTCCP was converted to the corresponding tetra-PEG derivative.

The reaction mixture was dissolved in 50 ml of water and the pH adjusted to neutral. Cycles of membrane ultrafiltration, using Centriprep™3 (Amicon) 15 ml concentrators removed most of the unreacted PEG. Final purification was achieved by size exclusion chromatography which involved passing the solution through a chromatographic column filled with Sephadex G-15. $^1H$ NMR analysis (DMSO-$D_6$) showed the presence of small amounts of unreacted PEG in the purified sample. The degree of purification was measured by quantitatively calibrated measurements of the light absorbtion.

EXAMPLE 6

Figure 5:
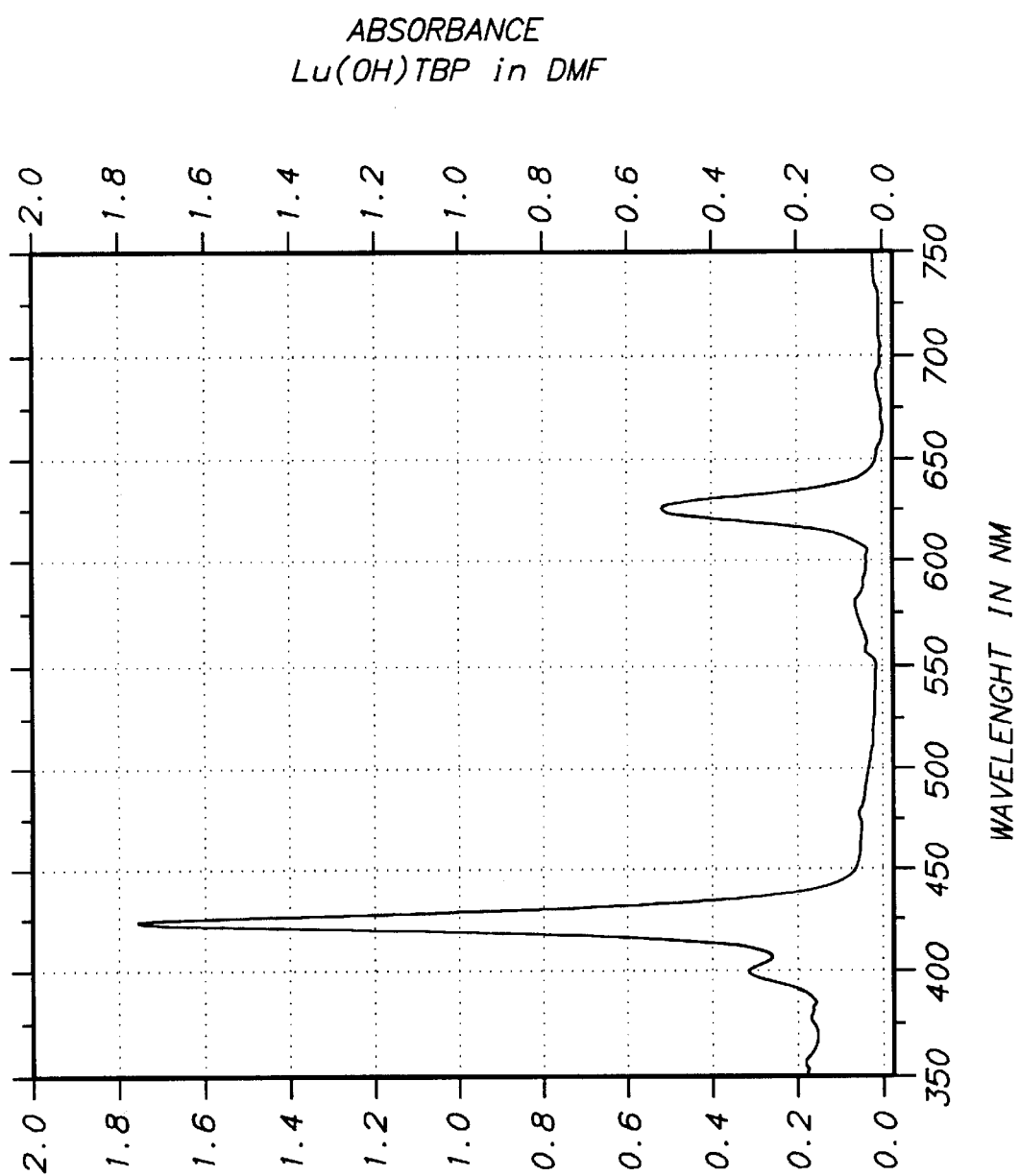
FIG. 5 is a graphical representation of the phosphorescent spectra of lutetium (hydroxy) meso-tetraphenyltetrabenzoporphyrin.
Figure 6:
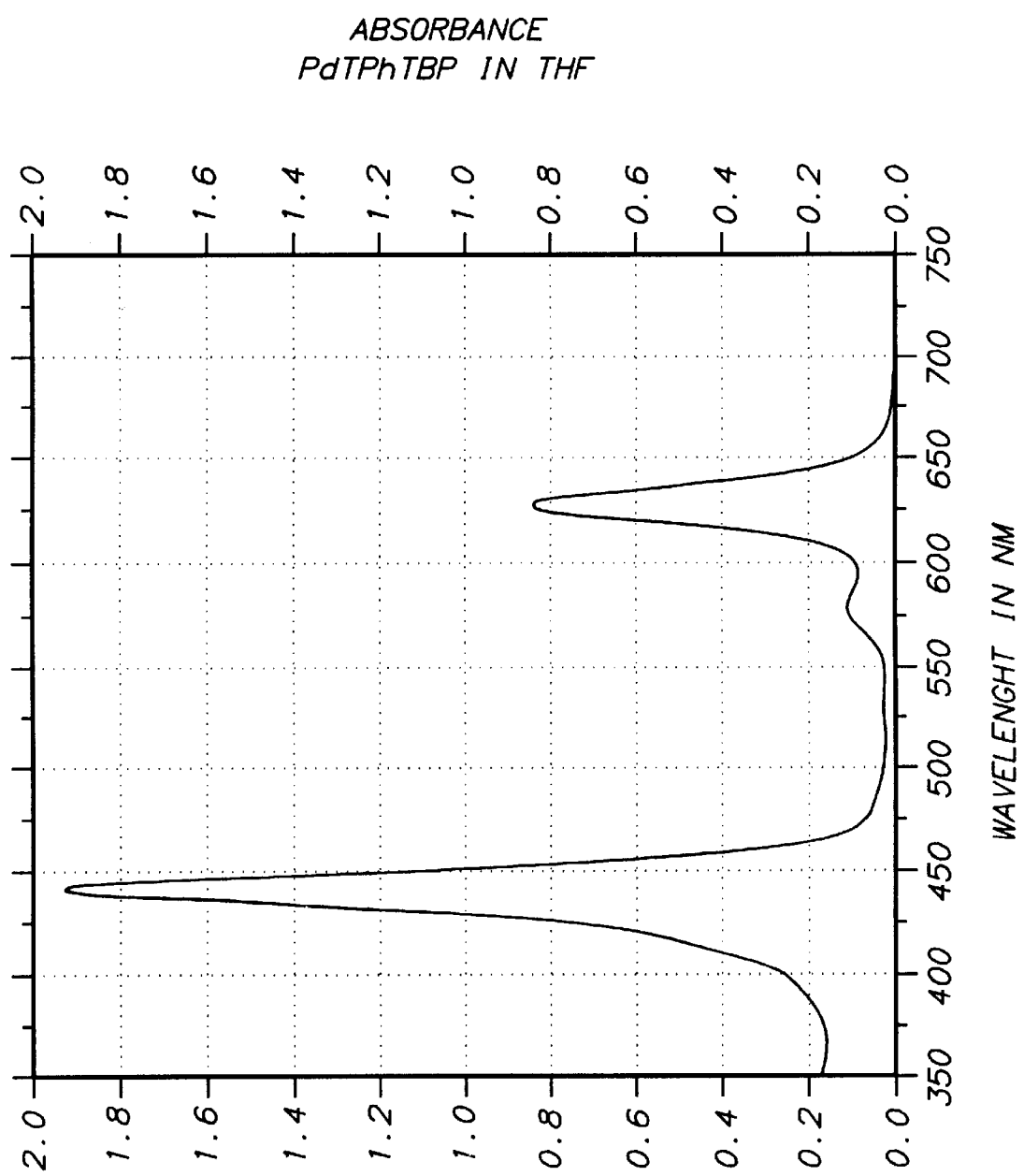
FIG. 6 is a graphical representation of the phosphorescent spectra of palladium meso-tetraphenyltetrabenzoporphyrin.

Phosphorescence of a series of metal-TBP compounds was detected using constant irradiation of samples with light wavelengths at their Q and Soret bands. To observe the phosphorescence phenomena and to record phosphorescence spectra, the samples were intensively deoxygenated. Accordingly, highly degassed dimethylformamide (DMF) or THF were used as solvents. The phosphorescence spectra of LuTPhTBP and PdTPhTBP are depicted in FIGS. 5 and 6, respectively.

The phosphorescent maxima of various compounds are tabulated in Table I below.

TABLE I

| Compound | Solvent | Soret band[a](nm) | Q-band (nm) |
|---|---|---|---|
| meso-tetraphenyltetrabenzoporphyrin compounds (TPhTBP) | | | |
| ZnTBP (Pyridine)2[b] | DMF | 425 | 624 |
| ZnTPhTBP (Pyridine)$_2$[c] | Acetone | 428 | 625 |
| PdTPhTBP | $CHCl_3$ | 420 | 610 |
| SnTPhTBP | Acetone | 438 | 642 |
| Lu(OH)TPhTBP | Acetone | 423 | 628 |
| Y(OH)TPhTBP | Acetone | 431 | 630 |
| La(OH)TPhTBP | DMF | 432 | 633 |
| PbTPhTBP | Acetone | 487 | 663 |
| PtTPhTBP | DMF | 437 | 630 |
| PdTPhTBP (glyc)$_4$[d] | water | 421 | 620 |
| PdTPhTBP (sulfonamide)$_4$[e] | water | 415 | 630 |
| PdTPhTBP (glucosamine)$_4$[f] | water | 409 | 615 |
| meso-tetraphenyltetranaphthoporphyrin compounds (TPhTNP) | | | |
| ZnTPhTNP (pyridine)$_2$[g] | DMF | 452 | 708 |
| La(OH)TPhTNP | DMF | 440 | 708 |
| Lu(OH)TPhTNP | DMF | 440 | 709 |
| PdTPhTNP | DMF | 415 | 694 |
| PtTPhTNP | DMF | 425 | 700 |

[a]Because Soret bands of MTPhTNP are usually split, average positions are given in the table.
[b]ZnTBP was isolated as the dipyridyl complex. It is contemplated that the nitrogen atoms of the pyridine moieties complex with the zinc atom.
[c]See above comments.
[d]Reaction product of PdTPhTBP($SO_2Cl$)$_4$ and glycine.
[e]Reaction product of PdTPhTBP($SO_2Cl$)$_4$ and 4-aminophenylacetic acid.
[f]Reaction product of PdTPhTBP($SO_2Cl$)$_4$ and D-glucosamine.
[g]See comments for footnote b.

Difficulty was encountered in measuring accurately quantum yields of phosphorescence inasmuch as photomultiplier response decreased greatly as wavelengths increased to greater than about 750 nm. However, the phosphorescence of the compounds in Table I was suitable to utilize the compounds to measure oxygen.

Lifetimes of deoxygenated samples of various Lu and Pd compounds in organic solvents is tabulated in Table II.

TABLE II

| Compound | A | B | C | D | E |
|---|---|---|---|---|---|
| PdTPhTBP | 784 | THF | 25 | 127 | — |
| LuTPhTBP | 807 | THF | 25 | 195 | — |
| PdTPhTNP | — | THF | 25 | 165 | — |
| LuTPhTNP | — | DMF | 25 | 172 | — |
| PdTPhTBP (glucosamine)$_4$[h] | — | Phy. sol.[i] | 38 | 431 | 194 |
| PdTPhTBP (glycine)$_4$[j] | — | Phy. sol. | 38 | 408 | 186 |
| PdTPhTBP (sulfonamide)$_4$[k] | — | Phy. sol.[l] | 38 | 377 | 185 |
| PdTCPP (PEG 4000)$_4$[m] | 690 | Phy. sol. | 38 | 457 | 301 |
| Pdmeso-Porph (PEG 1000)$_2$[n] | 695 | Phy. sol. | 38 | 757 | 597 |

A - Phosphorescence maximum (nm)

TABLE II-continued

| Compound | A | B | C | D | E |
| --- | --- | --- | --- | --- | --- |

B - Solvent
C - Temperature (° C.)
D - Phosphorescent lifetime at zero-oxygen concentration ($\mu s$)
E - Quenching constant at a temperature of 38° C. (Torr$^{-1}$s$^{-1}$)
[h]See footnotes for Table I.
[i]Aqueous solution containing: NaCl (0.12 M); Glucose (60 mM); Catalase; Glucosoxidase; Buffers: MOPS (10 mM), TrisBase (10 mM), Hepes (10 mM) (pH 7.0).
[j]See footnotes for Table 1.
[k]See footnotes for Table 1.
[l]The same solution as footnote i except pH was adjusted to 7.4.
[m]Pd meso-tetra(4-carboxyphenyl)porphyrin liganded with poly(ethylene glycol) (Avg. MW 4000).
[n]Pd meso-porphyrin liganded with poly ethylene glycol) (Avg. MW 1000).

Analysis of the foregoing data indicates that extension of the aromatic skeleton of porphyrin molecules moves the absorption and phosphorescent maxima further into the near infra-red region. Metal derivatives of TNP compounds show narrow absorption Q bands in the 640–720 nm region.

The positions of the absorption bands of MTBP and MTNP compounds permits use of laser diodes as excitation light sources. These diodes can be used to generate short, intense monochromatic light pulses. For example, currently available laser diodes emit at wavelengths as short as 630 nm with particularly powerful diodes from about 660–720 nm. Alternatively, for emission wavelengths greater than about 850 nm, photomultipliers, which are currently used as detectors, could be replaced by photodiodes which are more sensitive in the near infra-red region.

EXAMPLE 7

This example is directed to tetraanthraporphyrin (TAP) compounds.

The optical properties of metallotetraantraporphyrins are similar to those of TNP and TBP compounds except that the maximum absorptions and phosphorescences are shifted further to the red region of the infra-red spectra. The absorption bands lie in the 700–850 nm region. Applicants contemplate that in view of the almost parallel shift of absorption and emission maxima in the above porphyrin compounds, the metallotetraantraporphyrin compounds have a phosphorescence in the region from 820–1200 nm. Although these bands are currently more difficult to measure due to the relative lack of good light sensors at these wavelengths, it is contemplated that rapid technological advances in sensor design will render these compounds suitable for oxygen sensing, particularly in tissue of living animals.

The present invention has been described in accordance with the above detailed preferred embodiments. It is to be appreciated that other embodiments may fulfill the spirit of the present invention and that the true nature and scope of the present invention is to be determined with reference to the claims appended hereto.

What is claimed is:

1. A compound for the measurement of oxygen in living tissue comprising a substituted porphyrin which is capable of absorbing an amount of energy and subsequently releasing said energy as phosphorescent light, said substituted porphyrin having an absorption band at a wave-length in the near infra-red region in living tissue and said phosphorescence being quenched by molecular oxygen, said substituted porphyrin being soluble in an aqueous solution.

2. The compound of claim 1 wherein said compound has an absorption band at a wavelength of greater than about 600 nm.

3. The compound of claim 1 wherein said compound has an emission band at a wavelength in the near infra-red window of living tissue.

4. The compound of claim 3 wherein said compound has an emission band at a wavelength of greater than about 600 nm.

5. The compound of claim 3 wherein said absorption and emission bands are located in the range from about 600 nm to about 1300 nm.

6. The compound of claim 2 wherein said absorption band ranges from about 600 to about 640 nm.

7. The compound of claim 2 wherein said absorption band ranges from about 640 to about 720 nm.

8. The compound of claim 1 wherein said porphyrin is a metalloporphyrin.

9. A compound of claim 1 which is capable of phosphorescing and which has the formula

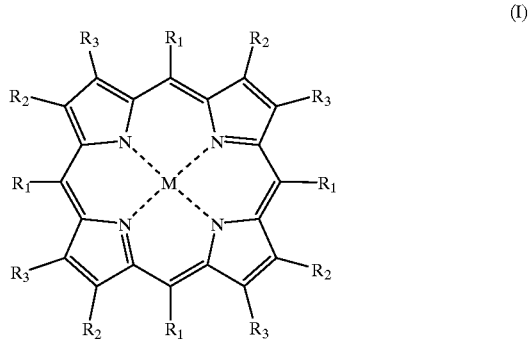

(I)

wherein:
$R_1$ is 2(3)-substituted aryl;
$R_2$ and $R_3$ are independently hydrogen or are linked together to form substituted or unsubstituted aryl; and
M is $H_2$ or a metal, said substituent group rendering the compound soluble in an aqueous solution.

10. The compound of claim 9 wherein M is a metal selected from the group consisting of Zn, Al, Sn, Y, La, Lu, Pd, Pt and derivatives thereof.

11. The compound of claim 10 wherein said derivatives are selected from the group consisting of LuOH, Pd, LaOH or Pt.

12. The compound of claim 9 wherein $R_2$ and $R_3$ are linked together to form a benzo system.

13. The compound of claim 12 wherein said benzo is selected from the group consisting of phenyl, naphthyl, anthryl, and phenanthryl.

14. The compound of claim 13 wherein the benzo of $R_1$ is a substituted phenyl.

15. The compound of claim 9 wherein said substituent group is a flexible, hydrophilic polymeric compound or a sugar compound.

16. The compound of claim 14 wherein said phenyl is further substituted with a substituent group at the 4-position.

17. The compound of claim 15 wherein said substituent is selected from the group consisting of a polyamide, polyethylene glycol, and polypropylene glycol.

18. The compound of claim 8 wherein the prophyrin is selected from the group consisting of tetrabenzoporphyrin, tetranapthoporphyrin, tetraanthraporphyrin, and derivatives thereof.

19. The compound of claim 18 wherein the metal is selected from the group consisting of Zn, Al, Sn, Y, La, Lu, Pd, Pt, and derivatives thereof.

20. The compound of claim 18 wherein the derivative is a meso-tetrapheylated compound.

21. The compound of claim 20 wherein the metalloporphyrin is (Pd) tetraphenyltetrabenzoporphyrin.

22. The compound of claim 20 wherein the metalloporphyrin is (Lu) tetraphenyltetranapwthoporphyrin.

23. The compound of claim 20 wherein the metalloporphyrin is (Pd) meso-tetra-(4-carboxylphenyl)porphyrin.

24. The compound of claim 23 which is modified with polyethylene glycol.

25. The compound of claim 14 wherein the porphyrin is phenyltetrabenzoporphyrin.

26. The compound of claim 20 wherein the porphyrin is meso-tetraphenyltetrabenzoporphyrin.

27. The compound of claim 20 wherein the porphyrin is meso-tetraphenyltetranaphthoporphyrin.

28. The compound of claim 17 wherein said substituent is selected from the group consisting of polyethylene glycol and polypropylene glycol.

29. The compound of claim 28 wherein said substituent is polyethylene glycol.

30. The compound of claim 28 wherein said substituent is polypropylene glycol.

31. The compound of claim 18 wherein the porphyrin is tetrabenzoporphyrin.

32. The compound of claim 31 wherein said substituent is selected from the group consisting of polyethylene glycol and polypropylene glycol.

33. The compound of claim 32 wherein said substituent is polyethylene glycol.

34. The compound of claim 32 wherein said substituent is polypropylene glycol.

35. The compound of claim 1 wherein said substituent is a flexible, hydrophilic polymeric compound.

36. A method for preparing a compound of claim 1 having the formula

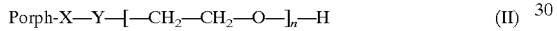

$$\text{Porph-X—Y—[—CH}_2\text{—CH}_2\text{—O—]}_n\text{—H} \quad (II)$$

wherein Porph is a porphyrin selected from the group consisting of dihydroporphyrin and metalloporphyrin, X is a chemical bond or a linking group selected from the group consisting of —CO— and —NHCH$_2$CO—, Y is a chemical bond or —O—, and n is an integer from about 8 to about 500, comprising:

(a) providing a compound of the formula

$$\text{Porph-X—Y—Z} \quad (III)$$

where Z is hydrogen, halo or hydroxy; and (b) reacting the compound of formula III with PEG at a temperature and for a time to provide a PEG-substituted porphyrin.

37. The method of claim 36 where said providing step comprises reacting a carboxy-substituted porphyrin with a halogenating agent selected from the group consisting of an inorganic halogenating agent and an organic halogenating agent.

38. The method of claim 37 wherein said halogenating agent is selected from the group consisting of thionyl chloride and oxalyl chloride.

39. The method of claim 36 comprising reacting the compound of formula III with PEG at a temperature of about room temperature to about the reflux temperature of PEG.

40. The method of claim 39 comprising reacting the compound of formula III with PEG at a temperature of about 100° C. to about 150° C.

41. The method of claim 36 comprising reacting the compound of formula III with PEG for about several hours to about several days.

42. The method of claim 41 comprising reacting the compound of formula III with PEG for about 24 hours.

43. A method for measuring oxygenation of living tissue comprising providing in vivo a phosphorescent compound comprising a substituted porphyrin having an energy absorption band at a wavelength in the near infra-red window of said tissue and being soluble in an aqueous medium and wherein said phosphorescence is quenched by molecular oxygen, causing said compound to phosphoresce and observing quenching by oxygen in said tissue of said phosphorescing compound.

44. The method of claim 43 comprising providing in vivo a compound selected from the group consisting of tetrabenzoporphyrin, tetranaphthoporphyrin, tetraanthraporphyrin and derivatives thereof.

45. The method of claim 44 comprising providing in vivo a compound having the formula

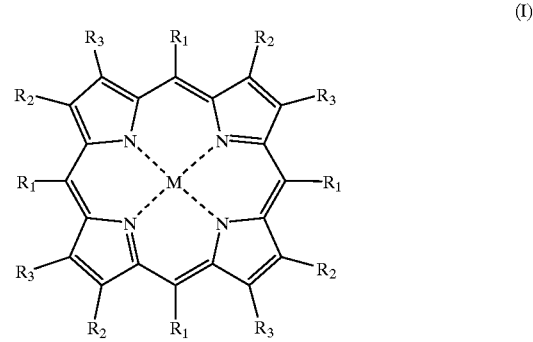

(I)

wherein:

R$_1$ is substituted or unsubstituted aryl;

R$_2$ and R$_3$ are independently hydrogen or are linked together to form an aryl group; and M is H$_2$ or a metal.

46. The method of claim 45 comprising diagnosing in the tissue of a patient a disease which causes an alteration of the oxygen pressure in said tissue.

* * * * *